US00PP26363P3

(12) United States Plant Patent
Austin

(10) Patent No.: US PP26,363 P3
(45) Date of Patent: Feb. 2, 2016

(54) ***ROSA HYBRIDA* SHRUB NAMED 'AUSPLUTO'**

(50) Latin Name: *Rosa hybrida*
Varietal Denomination: AUSpluto

(71) Applicant: David Austin Roses Ltd., Albrighton, Wolverhampton (GB)

(72) Inventor: David J. C. Austin, Wolverhampton (GB)

(73) Assignee: DAVID AUSTIN ROSES LTD, Albrighton, Wolverhampton (GB)

( * ) Notice: Subject to any disclaimer, the term of this patent is extended or adjusted under 35 U.S.C. 154(b) by 151 days.

(21) Appl. No.: 13/999,988

(22) Filed: Apr. 11, 2014

(65) Prior Publication Data

US 2015/0074860 P1 Mar. 12, 2015

(51) Int. Cl.
*A01H 5/02* (2006.01)

(52) U.S. Cl.
USPC ..... Plt./102
CPC ..... *A01H 5/0222* (2013.01)

(58) Field of Classification Search
USPC ..... Plt./102
CPC ..... A01H 5/0222; A01H 5/0216
See application file for complete search history.

*Primary Examiner* — Kent L Bell
(74) *Attorney, Agent, or Firm* — KPPB LLP

(57) ABSTRACT

A variety of rose plant of the shrub class, named 'AUSpluto'. The 'AUSpluto' is a variety of rose having very large flowers with a distinct two-tone coloration having rich yellow centers and pink outer petals with a fruity fragrance.

1 Drawing Sheet

Classification: The present invention relates to a new *Rosa hybrida* shrub of the market class 'English Rose'.

Variety denomination: The new plant has the varietal denomination 'AUSpluto'.

CROSS-REFERENCE TO RELATED APPLICATIONS

The current application claims priority to a European Community Plant Variety Application No. 2013/2365, filed Sep. 11, 2013, the disclosure of which is incorporated herein by reference.

ORIGIN OF INVENTION

This invention relates to a new and distinct variety of shrub rose plant named 'AUSpluto', which was originated from the cross-pollination of the two 'unnamed' and unpatented seedlings of *Rosa hybrida.*

BACKGROUND OF THE INVENTION

The primary objective of this breeding was to produce a variety of rose having very large flowers with a distinct two-tone coloration having rich yellow centers and pink outer petals with a fruity fragrance.

SUMMARY OF THE INVENTION

Among the features which distinguish the new variety from others presently available and commercial rose cultivars known to the inventor is the following combination of characteristics: very large yellow centered flowers with pink outer petals and a fruity fragrance.

Asexual reproduction of the new variety by budding as performed at Bowling Green Lane in Albrighton, Britain shows that the foregoing and other distinguishing characteristics come true to form and are established and transmitted through succeeding asexual propagations. 'AUSpluto' may be asexually propagated by budding. The budding successfully occurred on the plant/rootstock *Rosa* 'Inermis' for the observed plants.

COMPARISON WITH PARENTS

The seed and pollen parents of 'AUSpluto' are two unnamed seedlings. The new rose may be distinguished from its seed parent, by the following combination of characteristics: the seed parent is a deeply-cupped, pink bloom compared with the two-tone yellow and pink bloom of 'AUSpluto'. The new rose may be distinguished from its pollen parent, by the following combination of characteristics: the parent has characteristic hybrid tea blooms that are yellow compared with the loosely arranged petals and two-tone blooms of 'AUSpluto'.

COMPARISON WITH THE CLOSEST COMMERCIALLY AVAILABLE CULTIVAR

The closest commercially available cultivars to the new variety are the 'AUSlevity' (unpatented). The new rose may be distinguished from the 'AUSlevity' variety by the following combination of characteristics: the 'AUSlevity' has a similar yellow center bloom, but the outer petals are creamy white, whereas in 'AUSpluto' the outer petals are a deep pink. In addition, as the buds begin to open the 'AUSpluto' bloom first shows pink, while the 'AUSlevity' bloom first shows a yellow color.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (2001) except where common terms of color definition are employed.

DESCRIPTION OF THE NEW VARIETY

Observations of budded 'AUSpluto' specimens were made at the nursery in Albrighton, Wolverhampton, United Kingdom. The following description is of 6 year-old potted rose plants of the new variety grown indoors in a greenhouse in Albrighton, Britain in the month of June. Phenotypic expression may vary with environmental, cultural and climatic conditions, as well as differences in conditions of light and soil.

Flower characteristics:

*Blooming habit.*—Continuous. The number of blooms per plant during the growing season is profuse, but there are too many to count.

*Bud.*—Size: About 1.8 cm long and 1.6 cm in diameter when the petals start to unfurl. Form: The bud form is pointed ovoid. Color: When sepals first divide, the bud color is RHS 47B (red group). When half blown, the upper sides of the petals are RHS 12A (yellow group) and RHS 36A (red group) at the margin, and the lower sides of the petals are RHS 12A (yellow group) and RHS 36A (red group) at the margin. Calyx: Shape: star-shaped, folding back towards the stem when the flower is open. Length: 8 cm. Diameter: 8 cm. Sepals: Arrangement: Regular. Color: Upper Surface: green RHS 143C (green group). Lower Surface: green RHS 143C (green group) and RHS 47A (red group). Length: 2.9 cm. Width: 1 cm. Shape: Lanceolate. Surface texture: Upper Surface: Downy. Lower Surface: Glandular. Number: There are 0-2 very lightly appendaged sepals, and 3-5 unappendaged sepals with hairy edges. (That is, some blooms have no appendages on any of the sepals.) Receptacles: Color: RHS 144B (yellow-green group) with some RHS 47A (red group). Shape: funnel. Size: large and broad, about 12 mm high×16 mm wide. Surface: Smooth. Peduncle: Length: medium, averaging about 8 cm. Surface: Glandular. Color: RHS 144B (yellow-green group) with some RHS 47A (red group). Strength: Strong.

*Blooms.*—Size: Very large, average open diameter is about 11 cm. Borne: Mostly singly (1-4). (Note: the inflorescence when the shrub is growing naturally may hold between 1 and 4 blooms, and then has a flat shape. When grown commercially for cut-flower production the stems are disbudded to ensure the blooms are grown singly.) Stems: Strength: Strong, average length is about 60 cm. Diameter: 4 mm. Form: When first open, bloom is cupped. Permanence of bloom: outer petals curl back.

*Petalage.*—Number of petals under normal conditions: 87. Color: The upper sides of the petals are RHS 5A (yellow group). The reverse sides of the petals are RHS 6C (yellow group), and the base of the petals have no yellow spot. For the outer petals, which are distinctly different from the yellow petals making up the inner portion of the flower, the color is: upper and lower side: RHS 65A and 65B (red-purple group). The base of the outer petals are RHS 6C (yellow group). Variegations: None. Discoloration: The general tonality at the end of the first day is RHS 5A (yellow group), and at the end of the third day is RHS 5A (yellow group). Fragrance: Moderate. Character of fragrance: fruity.

*Petals.*—Texture: Satiny. Size: Width: 48 mm. Length: 60 mm. Surface: Smooth. Shape: Obovate. Margin: Strongly undulating. Apex Shape: Rounded with some notched. Petals are more frilly towards the center of the bloom. Base Shape: Obtuse. Form: Incurved. Arrangement: Informal. Petaloids: Number: 15. Color: RHS 5A (yellow group) Length: Varies between 1 to 7 cm. Width: Varies between 0.5 to 4 cm. Shape: Irregular obovate. Margin: Irregular. Persistence: Petals hang on and dry. Lastingness: On the plant: not tested. As a cut flower: About 9 days.

*Reproductive parts.*—Stamens: Number: 40. Length: 12 mm. Anthers: Length: 3 mm. Color: RHS 5A (yellow group). Arrangement: mixed with petaloids. Filaments: Color: RHS 13A (yellow group). Length: 12 mm. Pollen: Color: RHS 15A (yellow-orange group). Pistils: Number: 50. Length: 14 mm. Styles: Color: RHS 155C (white group) with RHS 63B (red-purple group) at tip. Length: 10-13 mm. Stigmas: Color: RHS 14B (yellow-orange group). Length: 1 mm. Hips: None Observed.

Plant characteristics:

*Plant form.*—Shrub, English Rose.

*Plant growth.*—Medium and upright.

*Age to maturity.*—One year.

*Mature plant.*—Height: 60 cm. Width: 45 cm.

*Rootstock.*—*Rosa* 'Inermis' for the observed plants.

*Foliage.*—Number: Leaflets on normal mid-stem leaves is: 5. Size: Large, about 19 cm long×14 cm wide. Quantity: Normal. Number of leaves per flowering stem is: 10. Color: New foliage: Upper side: RHS 146A (yellow-green group) overlaid with RHS 59A (red-purple group). Lower side: yellow/green RHS 183B (greyed-purple group). Old foliage: Upper side: RHS 147A (yellow-green group). Lower side: RHS 146B (yellow-green group) with RHS 183B (greyed-purple group).

*Leaflets.*—Size: About 7 cm long×5.5 cm wide. Shape: Pointed oval. Base Shape: Cordate. Apex Shape: Acuminate. Texture: Glossy. Edge: Serrated. Serrations: Double. Petiole: Color: RHS 144B (yellow-green group) with RHS 183B (greyed-purple group). Length: 5.5 cm. Width: 2 mm. Surface Texture: Rough. Petiole Rachis: Color: RHS 144B (yellow-green group) with RHS 183B (greyed-purple group). Underside: with some prickles and glandular. Stipules: Length: 3 cm, glandular. Color: RHS 144B (yellow-green group). Auricle: Shape: Lanceolate. Length: 10 mm. Width: 2 mm. Color: RHS 144B (yellow-green group). Vein Color: Same as leaf color. Venation Pattern: Reticulate.

*Wood.*—New Wood: Color: RHS 183B (greyed-purple group). Bark: Smooth. Old Wood: Color: RHS 147A (yellow-green group). Bark: Smooth.

*Branching habit.*—Number: 2. Lateral Branch Dimension: Length: 30 cm. Diameter: 4 mm.

*Stems.*—Mature Stem: Length: 60 cm. Diameter: 5 mm. Internode Distance: 6 cm. The above measurements are all variable, depending on growing conditions in a season. Stem Pubescence Present: No.

*Prickles.*—Quantity: On main canes from base: Many. Number per stem length: 50 per 10 cm. On laterals from main canes: Many. Number per stem length: 50 per 10 cm. Form: Deep concave. Length: 6 mm. Color when young: RHS 60B (red-purple group). Color when mature: RHS 199C (greyed-brown group).

*Small prickles.*—Quantity: Main stalk: None. Laterals: None.

*Disease resistance.*—Mildew: Resistant. Blackspot: Not tested. Rust:. Not tested.

*Pest resistance.*—Not tested.

*Winter hardiness.*—Not tested.

*Growing conditions.*—Normal greenhouse conditions.

What is claimed is:

1. A new and distinct variety of rose plant of the shrub class suitable for cut flower production, substantially as herein shown and described.

* * * * *

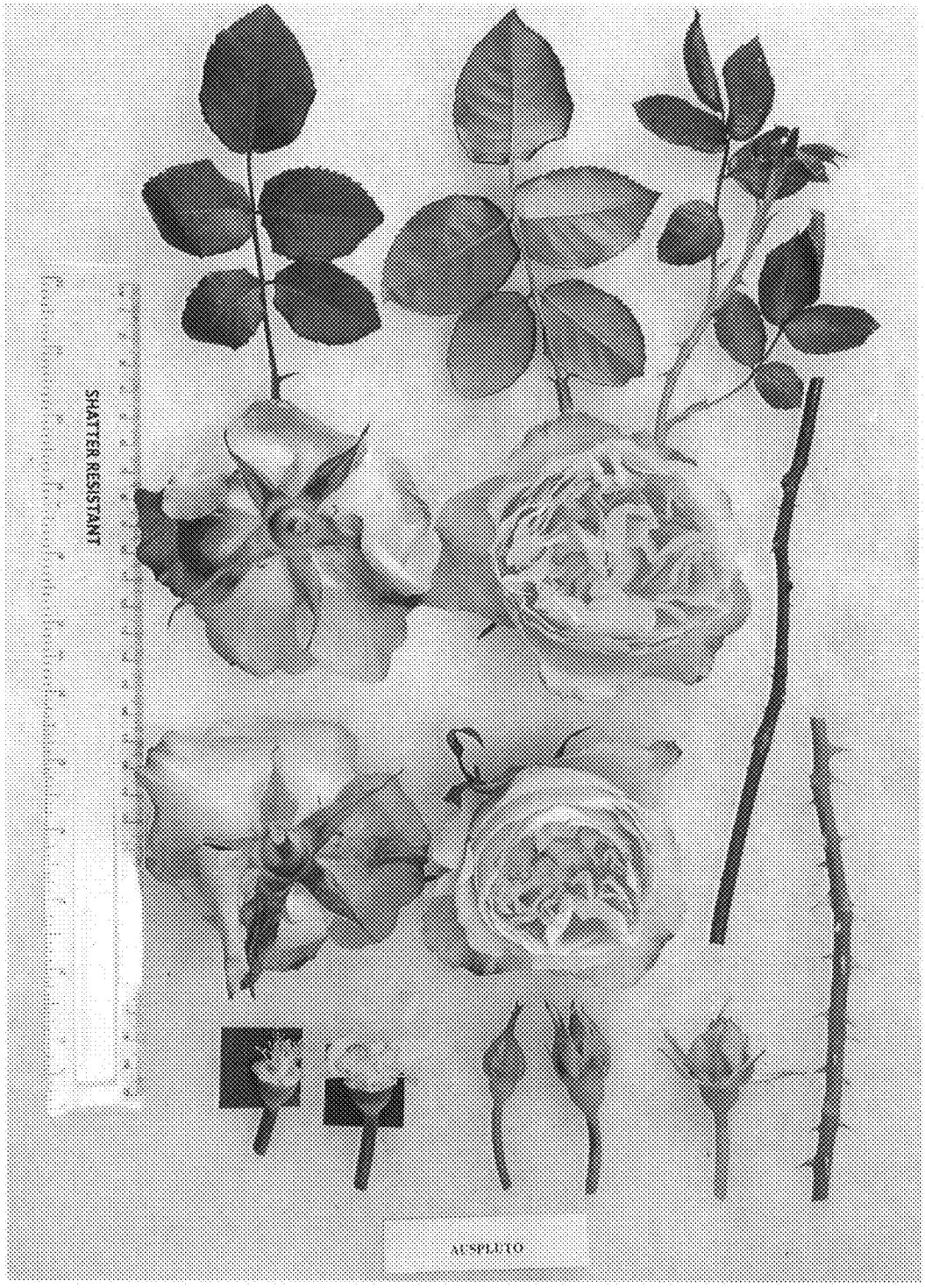
AUSPLETO
SHATTER RESISTANT